United States Patent [19]

McArthur et al.

[11] Patent Number: 5,795,321
[45] Date of Patent: Aug. 18, 1998

[54] IONTOPHORETIC DRUG DELIVERY SYSTEM, INCLUDING REMOVABLE CONTROLLER

[75] Inventors: William Allan McArthur, Highland Lakes, N.J.; Scott Edward Stropkay, Carlisle, Mass.; Marc Walter Tanner, London, United Kingdom

[73] Assignee: Becton Dickinson and Company, Franklin Lakes, N.J.

[21] Appl. No.: 316,655

[22] Filed: Sep. 30, 1994

[51] Int. Cl.$^6$ ............................................. A61N 1/30
[52] U.S. Cl. ................................................. 604/20
[58] Field of Search ........................ 604/19–20, 890.1, 604/289, 304; 607/3, 59, 149

[56] References Cited

U.S. PATENT DOCUMENTS

| | | |
|---|---|---|
| 4,708,716 | 11/1987 | Sibalis ............................................ 604/20 |
| 4,820,263 | 4/1989 | Spevak et al. . |
| 4,927,408 | 5/1990 | Haak et al. . |
| 4,942,883 | 7/1990 | Newman . |
| 5,084,008 | 1/1992 | Phipps . |
| 5,458,569 | 10/1995 | Kirk, III et al. . |
| 5,498,235 | 3/1996 | Flower . |
| 5,603,693 | 2/1997 | Frenkel et al. ............................... 604/20 |

FOREIGN PATENT DOCUMENTS

| | | |
|---|---|---|
| 0461680 | 12/1991 | European Pat. Off. . |
| 4028125 | 7/1991 | Germany . |
| 8602277 | 4/1986 | WIPO . |
| 9415669 | 7/1994 | WIPO . |

*Primary Examiner*—Mark Bockelman
*Assistant Examiner*—Ellen S. Tao
*Attorney, Agent, or Firm*—Allen W. Wark

[57] ABSTRACT

An iontophoretic drug delivery system of the present invention includes a multiple-pod housing, a controller, a power source and an electrode assembly in electrical contact with at least two reservoirs, with at least one of the reservoirs containing an active formulation to be delivered to an applied area of a patient. In the preferred embodiment, the housing includes three pods to more easily conform to the contours of the body, with two pods each including reservoirs and the electrode assembly, and the other pod including the controller.

2 Claims, 5 Drawing Sheets

IONTOPHORETIC DRUG DELIVERY SYSTEM, INCLUDING REMOVABLE CONTROLLER

FIELD OF THE INVENTION

The present invention generally relates to iontophoretic systems for delivering drugs or medicines to patients transdermally, i.e., through the skin, and more specifically relates to iontophoretic drug delivery systems for extended wear with respect to a single use and for repeated use with a removable controller.

BACKGROUND OF THE INVENTION

Transdermal drug delivery systems have, in recent years, become an increasingly important means of administering drugs. Such systems offer advantages clearly not achievable by other modes of administration such as avoiding introduction of the drug through the gastro-intestinal tract or punctures in the skin to name a few.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using, for example, iontophoresis, which according to Stedman's Medical Dictionary, is defined as "the introduction into the tissues, by means of an electric current, of the ions of a chosen medicament."

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes, i.e., an anode and a cathode. Usually, electric current is driven from an external supply into the skin at the anode, and back out at the cathode. Accordingly, there has been considerable interest in iontophoresis to perform delivery of drugs for a variety of purposes.

However, several disadvantages and limitations have been associated with the flexibility of the device, especially in situations where the device is worn for extended periods of time. For example, as a result prolonged use of the such devices, e.g., over a 24 hour period, they were prone to peeling and uneven distribution of current over the applied area. In addition, the bulkiness of such devices made them cumbersome and noticeable.

Thus, there has been a need for an iontophoretic drug delivery system which would eliminate the problems and limitations associated with the prior devices discussed above, most significant of the problems being flexibility. In addition, there has been a need for a device, which could utilize a reusable controller and provide a compact and inconspicuously worn device.

SUMMARY OF THE INVENTION

In contrast to the prior devices discussed above, it has been found that a iontophoretic drug delivery system particularly suited for application to the body, while providing direct contact even during prolonged use can be constructed in accordance with the present invention. In addition, the system of the present invention can be used with a reuseable controller to further reduce cost.

The iontophoretic drug delivery system of the present invention for delivering at least one active agent to an applied area of a patient, such as the skin, mucus membrane and the like, includes housing means having two or more electrically interconnected pods for containing electrode assembly means including at least two electrodes for driving the at least one active agent into the applied area of the patient along electrical field lines generated by the electrical current, a first reservoir situated in electrical communication with a first one of the electrodes and the first reservoir containing the at least one active agent to be delivered to the applied area of the patient, and a second reservoir situated in electrical communication with a second one of the electrodes and the second reservoir, with at least one of the pods for containing power means for supplying sufficient energy to drive the medicament into the patient, and controller means contained in one of the pods for controlling and monitoring the electrical energy delivered during operation so that the at least one active agent is delivered to the applied area of the patient approximate the first reservoir, whereby the housing conforms to the contours of the applied area.

In the preferred embodiment of the system, the pods are interconnected by a flexible web. In addition, the housing means includes an upper portion, a lower portion and an intermediate portion, with the intermediate portion including at least one tab for electrical interconnection with the power means.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

DETAILED DESCRIPTION OF THE PREFERRED EMBODIMENT

The iontophoretic drug delivery system of the present invention is illustrated in FIGS. 1–6, with the device generally designated 10.

Figure 1:
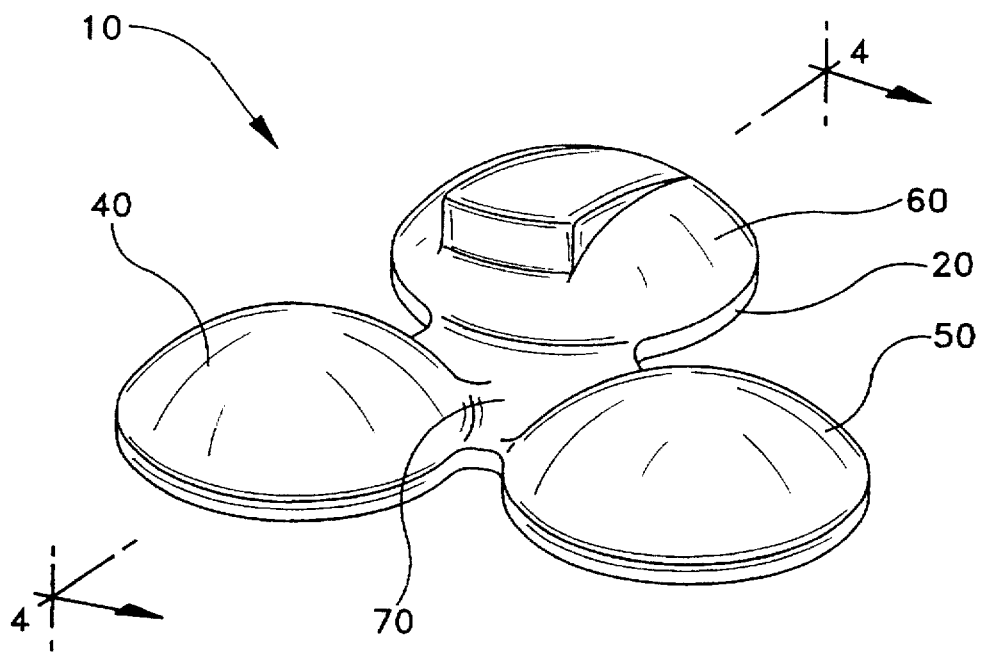
FIG. 1 is a perspective view of the iontophoretic system of the present invention.
Figure 2:
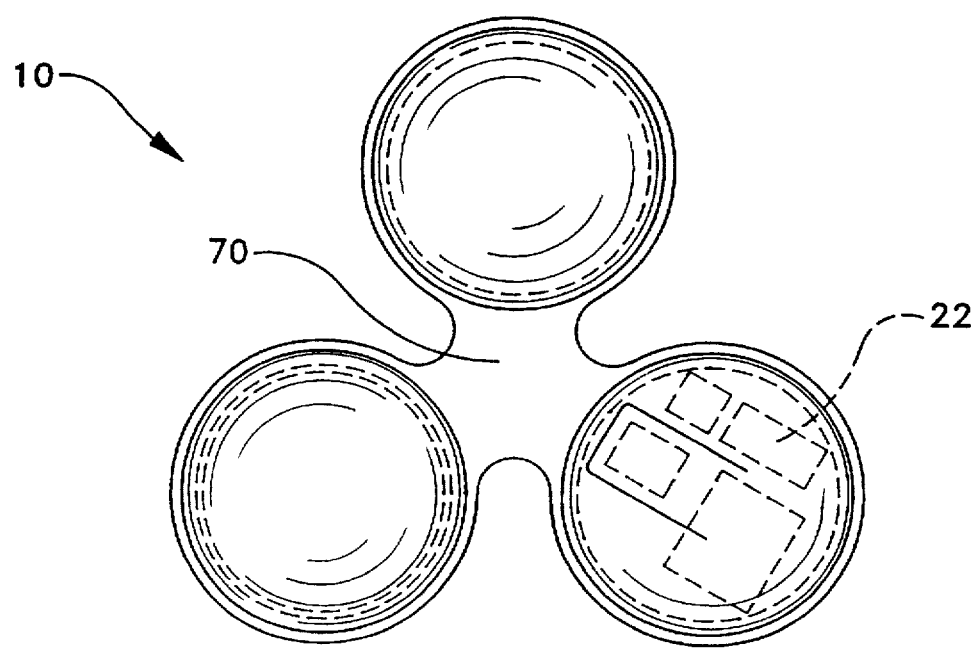
FIG. 2 is a plan view of the iontophoretic system illustrated in FIG. 1.
Figure 3:
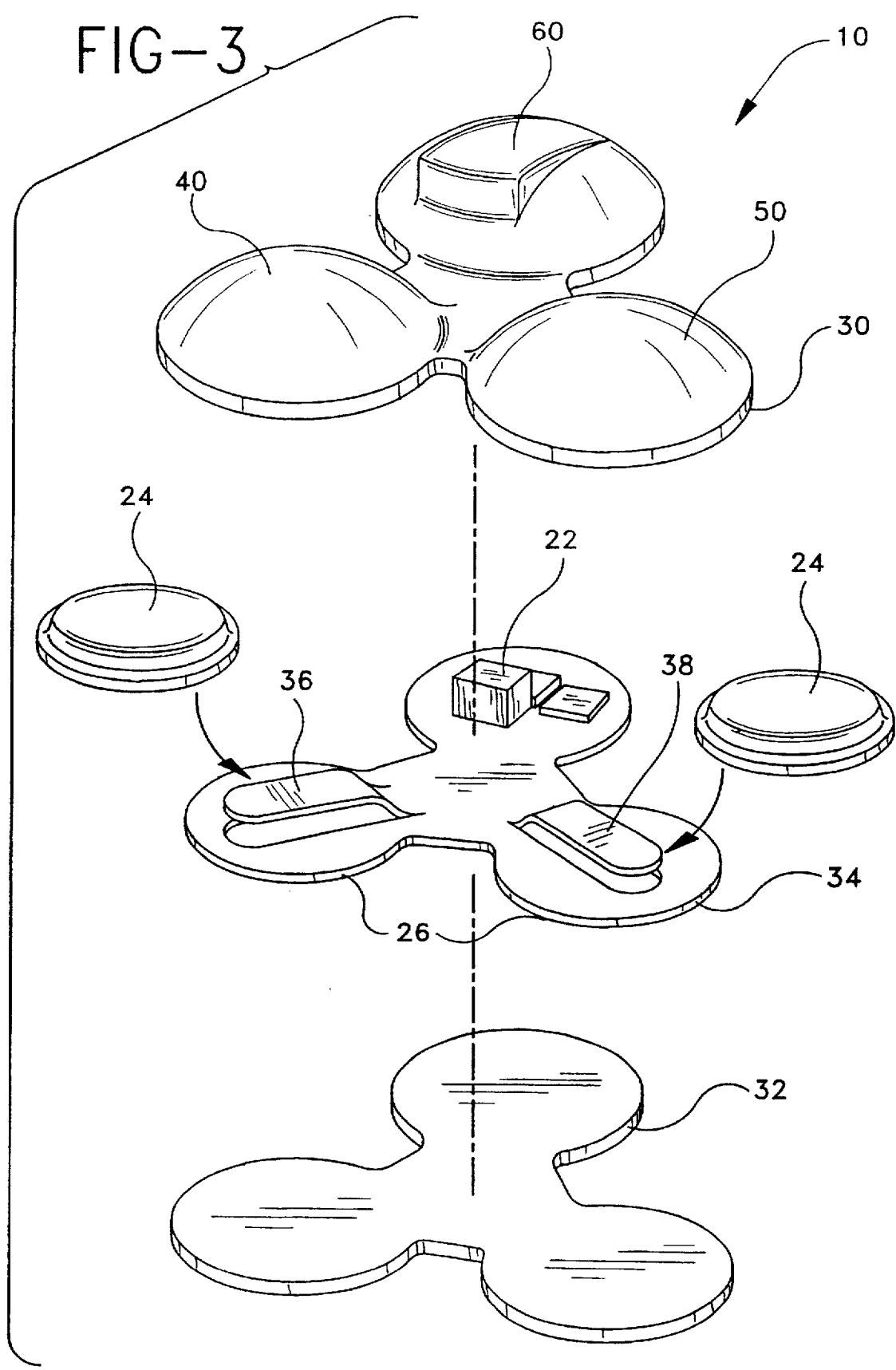
FIG. 3 is an exploded view of the iontophoretic system illustrated in FIG. 1.

Referring to FIGS. 1 and 2, and in greater detail in FIG. 3, the device 10 of the present invention includes a housing 20, a controller having an electronic array 22, at least one power source 24, an electrode assembly 26 having two or more electrodes for establishing an electric field between the electrodes for use in delivering at least one active agent iontophoretically to an applied area of the patient. It should be appreciated that the electrodes may be combined in the electrode assembly 26 or separately provided as is well known in the art.

As illustrated in FIGS. 1 and 2, and in greater detail in FIG. 3, the housing 20 includes an upper portion 30, a base or lower portion 32, and a intermediate portion 34. In addition, the housing 20 includes a number of pods, and preferably three pods 40, 50, 60 interconnected by a web 70 containing the circuit connecting the three pods. In the preferred embodiment, the intermediate portion 34 includes one or more locking tabs 36, 38 for engaging the power source, which may be split equally between the pods 40, 50 leaving only the electronic array, including logic circuit, in the other pod 60. Likewise, the power source may be incorporated within the electronic array.

Figure 4:
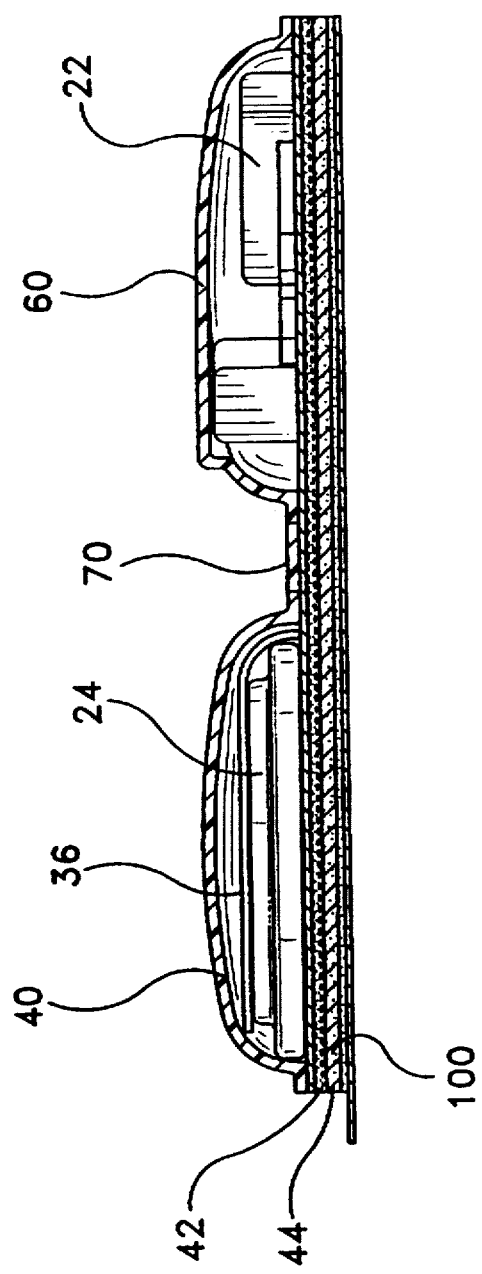
FIG. 4 is a cross-sectional view of the iontophoretic system illustrated in FIG. 1 taken along lines 4—4.

Also, the electrode assembly 26 is divided or otherwise separated into two portions, with the first pod 40 including an electrode 42 and a reservoir 44, with the reservoir 44 being situated adjacent to and in electrical communication with the electrode 42 as illustrated in FIG. 4. The second pod 50 also includes an electrode 52 and a reservoir 54, with the reservoir 54 being situated adjacent to and in electrical communication with the electrode 52. In this way, a lower surface of the intermediate portion 34 may include an electrode layer as disclosed, for example, in U.S. patent application Ser. No. 08/012,168, filed Feb. 2, 1993, now abandoned, the disclosure of which is hereby incorporated by reference in its entirety.

In the preferred embodiment, the first reservoir 44 holds at least one active agent, formulation, medication or drug 100, preferably in an ionized or ionizable form, to be delivered iontophoretically to the applied area of the patient. However, electrodes 42 and 52 may include an electrolyte, with the particular electrolyte not being essential to the present invention and merely a matter of choice. However, in this embodiment the electrolyte may include sodium chloride in an aqueous solution, matrix or the like. In situations where a polymer material or another material is used, it may also act as an adhesive, eliminating the need in prior devices for an adhesive layer or the like. However, it should be appreciated that in certain clinical applications it may be desirable to provide an adhesive layer under the web 70 in which case the pods can still be in planes that rotate slightly with respect to one another. Likewise, it may be desirable to forgo the adhesive under the web so that the planes can rotate and also flex in the distance between the centers of the pods to accommodate the skin as it stretches or muscles flex. Also, some elasticity or excess length can be incorporated. In this way, increased reliability of skin contact is achieved and maintained by the patient when wearing the device 10, especially for prolonged periods of time.

In the preferred embodiment, the pod 60 acts as the controller and includes the electronic array 22 as well as the power source 24 connected in a circuit with electrodes 42 and 52.

The controller, including the electronic array 22 and the battery 24, is connected in a circuit, with the electronic array 22, for example, also including a microprocessor, a dc/dc converter to increase the battery supply to approximately 30 volts, a current regulator which is controlled by the microprocessor and a timer or other means for monitoring the period of time the electrical current flows in a particular direction and/or the amount of current applied. In addition, current flowing through the reservoirs 44, 54 and the applied area can be controlled with a compliance voltage sufficient to account for variations in skin impedance and losses within the reservoirs. In addition, the electronic array 22 may include means for controlling the level of current to be applied over time and also for varying the current.

Accordingly, the device 10 can be utilized, for example, to vary the current $I_1$ during time period $T_1$, current $I_2$ during time period $T_2$, current $I_3$ during time period $T_3$, current $I_4$ during time period $T_4$, and current $I_5$ during time period $T_5$ and additional currents and time intervals as needed. Also, the controller may be adapted to include means for controlling the voltage V or the power I·V as well.

As is well known within the field, the device can be situated on the area of the patient to which the active agent is to be applied (the applied area) such as the skin and a voltage impressed across the electrodes 42 or 52 of the electrode assembly 28 to cause electrical current to flow through the skin of the patient to drive or otherwise transport the ionic active agent into the skin and the tissue to be absorbed by the body of the patient. The electric field lines are sufficiently long, however, so that the active agent is transported to the desired depth within the skin, and possibly to the vasculature, to provide the desired effect, e.g., therapeutic, anesthetic or diagnostic. It should also be appreciated that the multiple-pod construction of the housing permits the device of the present invention to easily conform to the contours of the body. In addition, the device may be used on other areas besides the skin, such as mucus membranes, depending upon the desired therapy and drugs to be delivered.

The active agent can have either a negative charge or a positive charge, but the active electrode must also be negatively or positively charged, respectively. Accordingly, where the active agent contained in the reservoirs 44 or 54 is positively charged, the electrical current flows from the first electrode 42 to the second electrode 52, and the first electrode 32 acts as the active electrode and the second electrode 52 acts as the return electrode, with the drug 100 being delivered to the applied area of the skin approximate the first electrode 42 and first reservoir 44.

In the preferred embodiment, the drug reservoir 44 includes the medicament 100 for delivery, which may contain, for example, either Alfentanil, Baclofen, Beclomethasone, Betamethasone, Buspirone, Cromolyn sodium, Bromocriptine, Calcitonin, Diclofenac, Diltiazem, Doxazosin, Droperidol, Encainide, Fentanyl, Granisetron, Haloperidol, Hydrocortisone, Indomethacin, Insulin, Isosorbide dinitrate, Ketoprofen, Ketorolac, Lidocaine, Lisinopril, LMW heparin, Melatonin, Methotrexate, Metoclopramide, Miconazole, Midazolam, Nicardipine, Oxybutynin, PGE 1, Piroxicam, Pramipexole, Prazosin, Scopolamine, Seglitide, Sufentanil, Terbutaline, Testosterone, Tetracaine, Tropisetron, Verapamil, Warfarin, Zacropride and Zatosetron, including derivatives, analogs and the like, which varying in duration for delivery from minutes to hours. In this way, the device can be used for delivering the medicament to the applied area for a short period of time or for extended periods of time. In addition, it should be appreciated that the dose of the medication can be varied depending upon the substance used.

Active agent, drug, formulation, medication, medicament and active compound have been used herein to mean any pharmaceutical agent, such as therapeutic compounds, diagnostic agents, anesthetic agents and the like.

Figure 5:
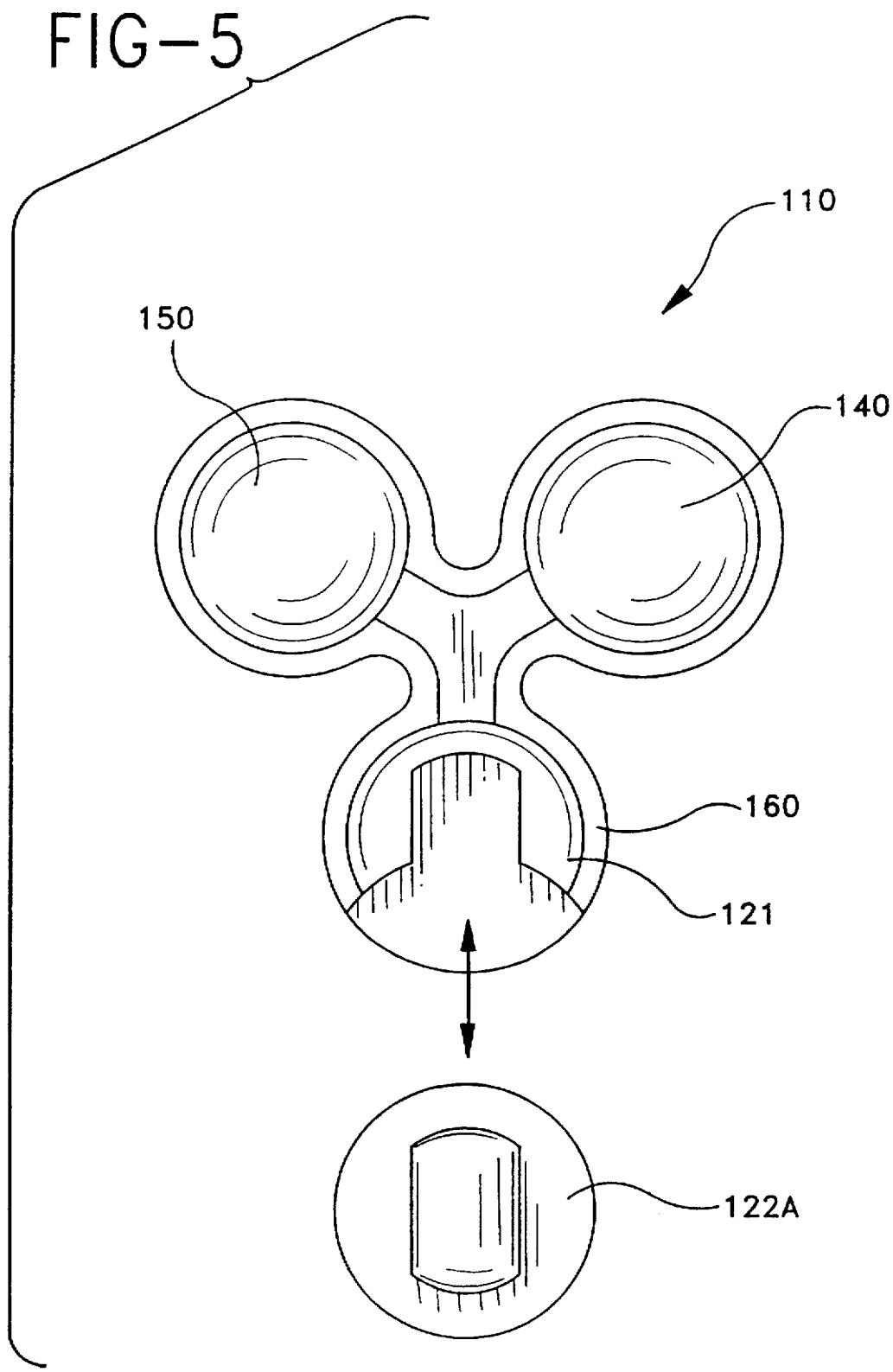
FIG. 5 is an exploded view of an alternative embodiment of the iontophoretic system of the present invention utilizing a reusable controller.

Referring to FIG. 5, an alternative embodiment of the device 110 is illustrated in which the housing 120 incudes three pods 140, 150 and 160, with the electronic array being contained in an controller 122A removably engageable by a sliding action in a receiving portion 121 formed in the housing. Likewise, referring to FIG. 6, yet another alternative embodiment of the device 210 is illustrated in which the housing includes two pods 240 and 260, with the electronic array being contained in an controller 222A removably engageable by a sliding action in a receiving portion 221 formed in the housing.

Figure 6:
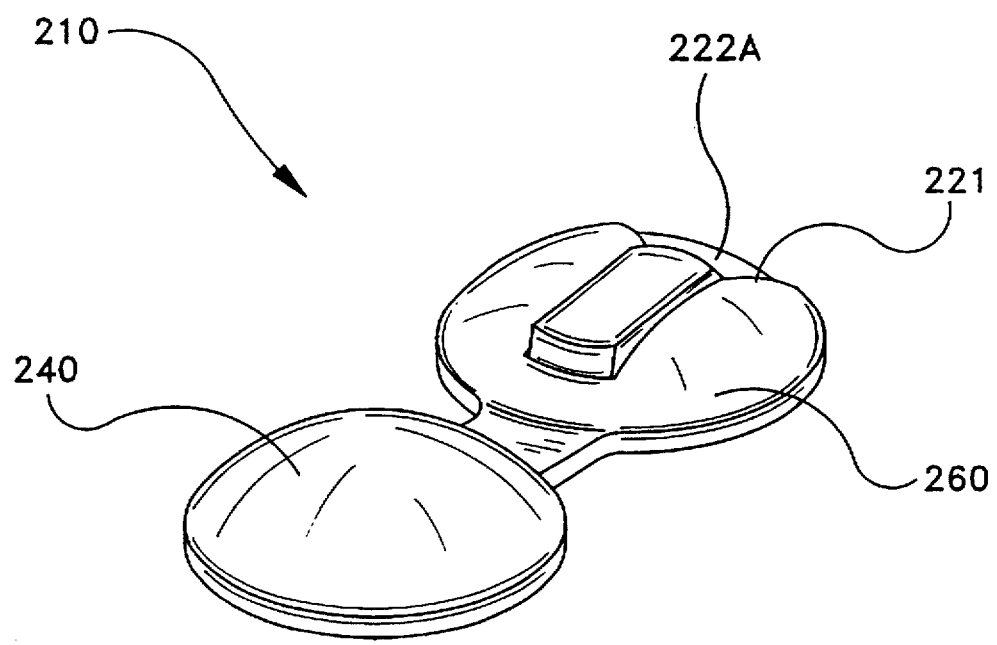
FIG. 6 is a perspective view of another alternative embodiment of the iontophoretic system of the present invention utilizing a reusable controller.

Accordingly, it should be appreciated that the pods can be arranged radially as illustrated in FIGS. 1–5 or some other orientation such as linearly, e.g., two or three in a row as illustrated in FIG. 6, to accommodate the specific requirements of the desired body location on which the device is to be applied.

Operation and Use

The operation of the system of the present invention will now be explained with reference to FIGS. 1–4, specifically that the device 10 including the various pods 40, 50, 60 interconnected by the flexible web 70 allows the device to be applied to the body with each of the pods not being influenced by the plane of attachment of the other pods. Thus, if the device were to be applied on a spherical surface, each pod would only have to be flexible enough to give good contact under itself.

In addition, while the device has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field.

While the preferred embodiments of the present invention have been described so as to enable one skilled in the art to practice the device of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. An iontophoretic drug delivery system for delivering at least one active agent to an applied area of a patient, such as the skin, mucus membrane and the like, comprising:

housing having an upper portion, a lower portion and an intennediate portion forming a first pod, a second pod and a third pod, with said pods being generally circular in shape and electrically interconnected by a flexible web, whereby said housing conforms to the contours of the applied area;

electrode assembly means for driving the at least one active agent into the applied area of the patient along electrical field lines generated by an electrical current, said electrode assembly means including at least a first electrode and a second electrode;

said first pod including said first electrode and a first reservoir situated in electrical communication with said first electrode, with said first reservoir containing said at least one active agent to be delivered to the applied area of the patient;

said second pod including said second electrode and a second reservoir situated in electrical communication with said second electrode;

said first pod and said second pod each including power means for supplying electrical current and sufficient energy to drive said at least one active agent into the patient;

said third pod including controller means for controlling and monitoring the electrical energy delivered by said power means during operation so that said at least one active agent is delivered to the applied area of the patient approximate said first reservoir; and interconnection means for releasably engaging said controller means.

2. An iontophoretic drug delivery system as defined in claim 1, wherein said intermediate portion includes at least one tab for electrical interconnection with said power means.

* * * * *